United States Patent [19]
Herbert

[11] Patent Number: 5,932,624
[45] Date of Patent: *Aug. 3, 1999

[54] VITAMIN SUPPLEMENT COMPOSITION

[76] Inventor: Victor D. Herbert, 440 E. 62nd St., Apt. 18D, NY, N.Y. 10021

[ * ] Notice: This patent issued on a continued prosecution application filed under 37 CFR 1.53(d), and is subject to the twenty year patent term provisions of 35 U.S.C. 154(a)(2).

[21] Appl. No.: 08/544,330

[22] Filed: Oct. 17, 1995

[51] Int. Cl.$^6$ ..................................................... A61K 31/00
[52] U.S. Cl. ...................... 514/904; 536/26.4; 544/250; 546/301
[58] Field of Search ........................ 514/904; 536/26.4; 544/250; 546/301

[56] References Cited

U.S. PATENT DOCUMENTS

| | | | |
|---|---|---|---|
| 2,748,054 | 5/1956 | Jurist | 514/52 |
| 4,053,593 | 10/1977 | Frumoff | 514/25 |
| 5,039,668 | 8/1991 | Colina | 514/52 |
| 5,135,851 | 8/1992 | Kajander | 435/34 |

OTHER PUBLICATIONS

Refsum, H. et al, Cancer Research, vol. 46(10), pp. 5385–5391, abstract only, Oct. 1986.
Drug Facts and Comparisons, edited by B.R. Olin et al, Wolters Kluwer Co. pp. 60–63, Feb. 1995.

*Primary Examiner*—Zinna Northington Davis
*Attorney, Agent, or Firm*—Elliot M. Olstein; Alan J. Grant

[57] ABSTRACT

A multiple vitamin supplement composition comprising folic acid and vitamin $B_{12}$ disclosed that is essentially free of antioxidants is disclosed. The multiple vitamin supplement composition may contain vitamin $B_6$. The multiple vitamin supplement composition is useful for lowering serum homocysteine levels to protect against related blood vessel disorders. Further disclosed is a method of preparing such a multiple vitamin supplement and a method of administration.

15 Claims, No Drawings

VITAMIN SUPPLEMENT COMPOSITION

Homocystinuria is characterized by high serum homocysteine levels and leads to blood vessel damage, excretion of homocysteine in the urine, mental retardation, ectopia lentis, sparse blonde hair, convulsive tendency, thromboembolic episodes, and fatty changes of liver and is associated with defective formation of cystathionine synthetase.

Homocysteine is a homolog of cysteine and is produced by the demethylation of methionine, and is an intermediate in the biosynthesis of cysteine from methionine via cystathionine by cystathioninase.

High serum homocysteine-related blood vessel damage may account for up to 20% of U.S. heart attacks, 40% of strokes and 60% of peripheral venous occlusions, in addition to those in the placenta associated with neural tube defects in about 2,000 infants a year.

It has recently been disclosed that the B vitamins, folic acid and vitamin $B_{12}$, by converting homocysteine to methionine, lower high serum homocysteine and thereby protect against high serum homocysteine-related blood vessel damage. The major sources of folic acid are foods that are often not ingested in sufficient amount, namely fresh fruits and vegetables, particularly the dark green leafy vegetables and orange juice. However, while vitamin $B_{12}$ is in all animal protein, including meat, fish, poultry, eggs, milk and milk products, there is none in anything that grows out of the ground.

Folic acid and vitamin $B_{12}$ are members of the vitamin B complex necessary for the normal production of red blood cells. Folic acid is present in peptide linkages in high quantities in liver, green vegetables and yeast. Vitamin $B_{12}$ is present in high quantities in liver and other animal products.

Many plant and animal tissues contain folic acid as reduced methyl or formyl polyglutamates. Folates act as co-enzymes for processes in which there is transfer of a 1-carbon unit, as in purine and pyrimidine nucleotide biosynthesis, amino acid conversions such as histidine to glutamic acid and generation and use of formate. Absorption takes place in the small intestine. In the gut epithelial cells, polyglutamates are reduced to dihydro- and tetrahydrafolates, and absorbed bound to protein and transported in blood serum as methyl tetrahydrafolate. Some absorbed folate is excreted in the bile and re-absorbed, together with an amount not absorbed and excreted in the stool.

Vitamin $B_{12}$ is necessary for taking a one-carbon unit from folic acid and delivering it to homocysteine to convert homocysteine to methionine. Vitamin $B_{12}$ is necessary for normal nerve function as well as for blood formation.

Vitamin $B_6$ is involved in a different pathway for getting rid of excess homocysteine, which pathway is usually less important than the $B_{12}$-folate dependent pathway.

Vitamin supplements containing Folic Acid and or vitamin $B_{12}$ and or Vitamin $B_6$ are known, however, such supplements contain other vitamins, phytochemicals and minerals such as iron and copper, or other antioxidant substances which destroy some of Vitamin $B_{12}$ and also some of the folic acid.

In accordance with an aspect of the present invention there is provided a multiple vitamin supplement composition comprising folic acid and vitamin $B_{12}$ that is essentially free of antioxidants.

In accordance with another aspect of the present invention there is provided a multiple vitamin supplement composition comprising folic acid, vitamin $B_{12}$ and vitamin $B_6$ that is essentially free of antioxidants.

In accordance with another aspect of the present invention there is provided a method of administering a multiple vitamin supplement composition for lowering high serum homocysteine levels to protect against the incidence of heart attack and other blood vessel related disorders.

In accordance with another aspect of the present invention there is provided a method of preparing a multiple vitamin supplement composition comprising folic acid and vitamin $B_{12}$ that is essentially free of antioxidants.

In accordance with another aspect of the present invention there is provided a method of preparing a multiple vitamin supplement composition comprising folic acid, vitamin $B_{,2}$ and vitamin $B_6$ that is essentially free of antioxidants.

In accordance with the primary aspect of the present invention there is provided a multiple vitamin supplement composition comprising folic acid and vitamin $B_{12}$. The composition may also contain vitamin $B_6$, wherein the composition is essentially free of antioxidants.

It has been shown that folic acid and vitamin $B_{12}$ each have the ability to protect against high serum homocysteine-related blood vessel damage, as in some circumstances, does vitamin $B_6$. High homocysteine levels also activate lipoprotein—little "a" to promote heart attacks.

Folic acid supplements taken alone are unsafe since they allow unrecognized genetically predisposed vitamin $B_{12}$ deficiency to produce irreversible nerve damage in susceptible populations. These susceptible populations consist of the elderly and women of African American descent in their child-bearing years. Accordingly, the multiple vitamin supplement composition of the present invention comprises folic acid and vitamin $B_{12}$, and may also contain vitamin $B_6$. The addition of vitamin $B_{12}$ lowers to normal the vitamin $B_{12}$-deficiency-produced high serum homocysteine found in millions of the elderly.

Vitamin $B_6$, the other B vitamin involved in homocysteine metabolism is also added to the multiple vitamin supplement of the present invention. The addition of vitamin $B_{12}$ and vitamin $B_6$ further metabolizes homocysteine and lowers serum homocysteine levels.

In a preferred embodiment, the multiple vitamin supplement of the present invention contains 500 micrograms of folic acid, 25 micrograms of vitamin $B_{12}$ and 10 milligrams of vitamin $B_6$.

The present invention departs from the prior art in the discovery that the multiple vitamin supplement composition as described above must be essentially free of antioxidants. Antioxidants, including but not limited to other vitamins, minerals such as iron and copper, and other phytochemicals, destroy not only the vitamin $B_{12}$ in the multiple vitamin supplement but also some of the folic acid in the supplement once the vitamin dissolves in the alimentary tract.

By "essentially free" it is meant that the vitamin composition of the present invention must not contain an amount of antioxidants which would tend to damage and inactivate some of the vitamin $B_{12}$ and/or folic acid of the vitamin supplement. The presence lower amounts of antioxidants would not render the vitamin composition of the present invention ineffective or of reduced effectiveness.

The components of the multiple vitamin supplement of the present invention are co-enzymes which act in accordance with methionine synthetase and cystathioninase and facilitate the production of methionine and cysteine from homocysteine. This lowers the serum level of homocysteine and the high level of heart attacks and other vascular damage associated therewith. The presence of antioxidants in the vitamin composition tends to inactivate the vitamin $B_{12}$ and folic acid components of the vitamin composition once the vitamin composition is processed in the alimentary tract.

Therapeutic treatment with the multiple vitamin supplement of the present invention may involve administration to persons prophylactically, that is to prevent, retard or reduce the severity of future occurrence of the disease or its clinical manifestations.

The multiple vitamin supplement composition of the present invention contains a therapeutically effective amount of folic acid, vitamin $B_{12}$ and may or may not also contain vitamin $B_6$ with the composition being essentially free of antioxidants. The vitamin composition may be administered with a pharmaceutically acceptable carrier. A pharmaceutically acceptable carrier may be any compatible, non-toxic, non-antioxidant substance suitable to deliver the components. The supplement may contain other pharmaceutically acceptable substances as required to approximate physiological conditions such as a pH adjusting and buffering agent, disbursing agents, toxicity adjusting agents, flavoring agents and like. The concentration of the components in these formulations may vary and will be selected primarily on the particular dosage and mode of administration selected. Methods for preparing supplements are well-known or will be apparent to those skilled in the art and are described in more detail in, for example, *Remington's Pharmaceutical Science,* 15th ed., Mack Publishing Company, Easton, Pa.

The supplement is useful for oral administration. The supplement may be formulated in a variety of dosage forms, such as tablets, capsules, oral solutions or suspensions.

Preferably, the supplement is administered orally. For oral administration, solid or fluid dosage forms can be prepared. For preparing solid compositions such as tablets, the components are mixed with conventional ingredients, such as talc, magnesium stearate, and functionally similar materials, as pharmaceutical carriers. Capsules are prepared by mixing the components with an inert pharmaceutical diluent and filling the mixture into a hard gelatin capsule. Soft gelatin capsules are prepared by machine encapsulation of a slurry of the components with an acceptable vegetable oil, light liquid petrolatum or other inert oil. Fluid unit dosage forms for oil administration such as serum and suspensions can be prepared. The components may be dissolved in an aqueous vehicle together with sugar, sweetening and flavoring agents and preservatives to form a serum. Suspensions can be prepared with an aqueous vehicle and a disbursing agent such as acacia, tragacanth, methylcellulose and the like. In accordance with the invention, any carrier, filler or other substance associated with the components of the invention used to prepare a tablet, capsule or the like must be essentially free of anti-oxidants.

In an alternate embodiment of the present invention, separate vitamin composition may be prepared in accordance with the invention by the methods described above with each containing only Folic acid or Vitamin $B_{12}$. These tablets are essentially free of anti-oxidant substances. In this manner, one or the other component of Folic acid or Vitamin $B_{12}$ can be taken alone such that a user, or their physician, may have more control over the quantity of intake of Folic Acid or Vitamin $B_{12}$, without be forced to also alter the level of intake of the other.

The compositions containing the multiple vitamin supplement components may be administered for the therapeutic treatment of high serum homocysteine disorders, including prophylactic treatment. In treatment of patients diagnosed with high serum homocysteine levels, the supplement may be administered to a person in an amount sufficient to reduce serum homocysteine levels to normal. In prophylactic treatment, the supplement may be administered to a person who may be at risk of having a high serum homocysteine blood vessel related disorder, but has not been diagnosed as having such an disorder. An amount adequate to accomplish any of these effects is referred to as a "therapeutically effective" amount. Unit dosages effective for this use will depend upon the severity of the disorder and the general state of the person's health, but will generally range from 300 to about 2,000 micrograms of folic acid, 25 to about 1,000 micrograms of vitamin $B_{12}$, and 5 to about 20 milligrams of vitamin $B_6$, with 500 micrograms of folic acid, 25 micrograms of vitamin $B_{12}$ and 10 milligrams of vitamin $B_6$ being preferred. The multiple vitamin supplement may be administered in dosages and over a period of time with a frequency and duration sufficient to yield a "therapeutically effective" amount, i.e., an amount sufficient to reduce serum homocysteine levels to normal.

What is claimed:

1. A vitamin or supplement composition adapted for administration to a human, the active components thereof consisting essentially of a member selected from the group consisting of:

(a) folic acid, and vitamin $B_{12}$;

(b) folic acid, vitamin $B_{12}$, and vitamin $B_6$;

(c) folic acid, vitamin $B_{12}$, and a non-antioxidant vitamin; and (d) folic acid, vitamin $B_{12}$, and non-antioxidant vitamins, said composition being essentially free of anti-oxidants.

2. A composition according to claim 1, wherein said member is:

folic acid, vitamin $B_{12}$ and vitamin $B_6$.

3. The composition of claim 2 in a unit dose form, said composition comprising:

500 micrograms of folic acid and 25 micrograms of vitamin $B_{12}$.

4. The composition of claim 2 in a unit dose form, said composition comprising:

500 micrograms of folic acid, 25 micrograms of vitamin $B_{12}$, and 10 micrograms of vitamin $B_6$.

5. A vitamin composition adapted for administration to a mammal comprising:

folic acid, said composition being essentially free of additional vitamins other than a B vitamin or B vitamins and essentially free of antioxidants, wherein said composition does not include amino acid supplements or an antimicrobial agent.

6. The composition of claim 1 in a unit dose form, said composition comprising:

500 micrograms of folic acid and 25 micrograms of vitamin $B_{12}$.

7. The composition of claim 1 in a unit dose form, said composition comprising:

500 micrograms of folic acid, 25 micrograms of vitamin $B_{12}$, and 10 micrograms of vitamin $B_6$.

8. A vitamin composition according to claim 1, wherein said composition is also free of any nutrient minerals.

9. A vitamin composition according to claim 2, wherein said composition is also free of any nutrient minerals.

10. A vitamin composition according to claim 11, wherein said composition is also free of any nutrient minerals.

11. A vitamin composition according to claim 12, wherein said composition is also free of any nutrient minerals.

12. The composition of claim 1, said composition comprising from 300 to 2000 micrograms of folic acid and from 25 to about 1000 micrograms of vitamin $B_{12}$.

13. The vitamin composition of claim 12, said composition further comprising from 5 to about 20 micrograms of vitamin $B_6$.

14. The vitamin composition of claim 12, said composition comprising 500 micrograms of folic acid and 25 micrograms of vitamin $B_{12}$.

15. The vitamin composition of claim 13 said composition further comprising 10 micrograms of vitamin $B_{12}$.

* * * * *

UNITED STATES PATENT AND TRADEMARK OFFICE
CERTIFICATE OF CORRECTION

PATENT NO. : 5,932,624
DATED : August 3, 1993
INVENTOR(S) : Victor D. Herbert

It is certified that error appears in the above-identified patent and that said Letters Patent is hereby corrected as shown below:

In the Claims:

At column 4, line 43, in claim 4, delete "micrograms" and insert therefor "milligrams"

At column 4, line 64, in claim 10, delete "claim 11" and insert therefor "claim 5"

Signed and Sealed this

Twentieth Day of June, 2000

Attest:

Q. TODD DICKINSON

*Attesting Officer*  *Director of Patents and Trademarks*